United States Patent [19]

Christensen

[11] Patent Number: 4,461,300

[45] Date of Patent: Jul. 24, 1984

[54] BONE AND TISSUE HEALING DEVICE INCLUDING A SPECIAL ELECTRODE ASSEMBLY AND METHOD

[75] Inventor: James M. Christensen, San Diego, Calif.

[73] Assignee: Sutter Biomedical, Inc., San Diego, Calif.

[21] Appl. No.: 340,521

[22] Filed: Jan. 18, 1982

[51] Int. Cl.³ ............................ A61N 1/04; A61N 1/18
[52] U.S. Cl. .................................. 128/419 F; 128/784
[58] Field of Search ............ 128/419 F, 82.1, 784–786

[56] References Cited

U.S. PATENT DOCUMENTS 3,842,841 10/1974 Brighton et al. ................. 128/419 F
3,918,440 11/1975 Kraus ................................. 128/419 F

FOREIGN PATENT DOCUMENTS 60500 3/1975 Australia ........................ 128/419 F

OTHER PUBLICATIONS

Zimmer–U.S.A., Lit. No. B-2360-1, 1979.
Zimmer–U.S.A. Product Encyclopedia, B44, Jun. 1978.

Primary Examiner—Lee S. Cohen
Attorney, Agent, or Firm—Flehr, Hohbach, Test, Albritton & Herbert

[57] ABSTRACT

A portable device used for expediting the healing of bone or soft tissue fractures or defects in a patient is disclosed herein and utilizes at least one cathode electrode, an anode electrode and a circuit arrangement for applying a regulated flow of current between the electrodes and through the fracture or defect site. A specifically designed electrode assembly including the cathode electrode is also disclosed herein along with a particular technique for placing the cathode electrode in position at the fracture or defect site.

11 Claims, 6 Drawing Figures

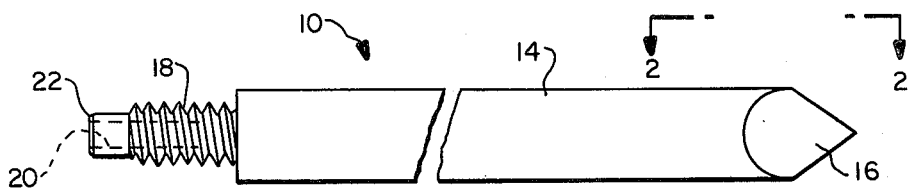
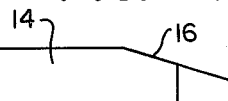
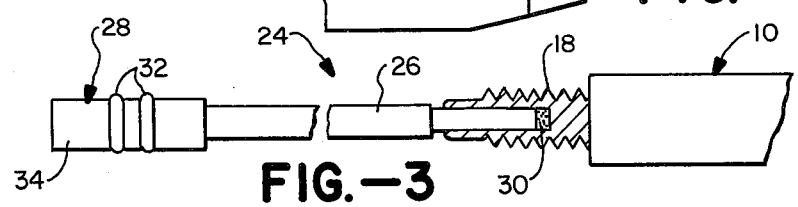
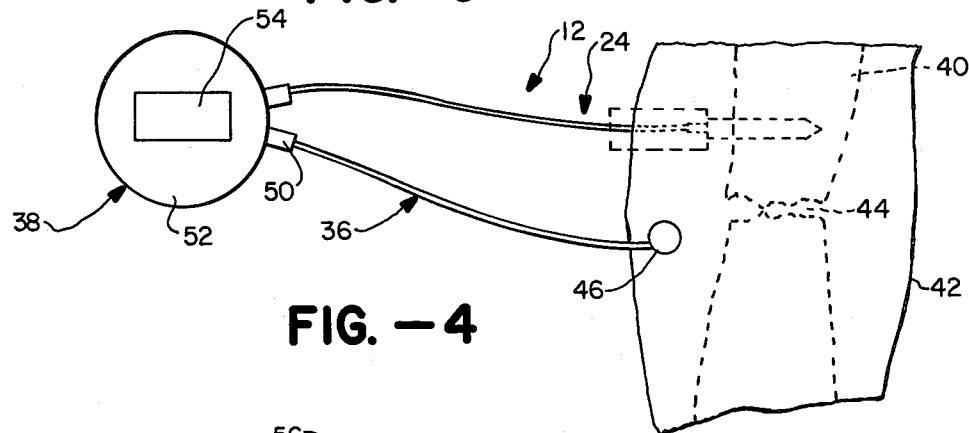
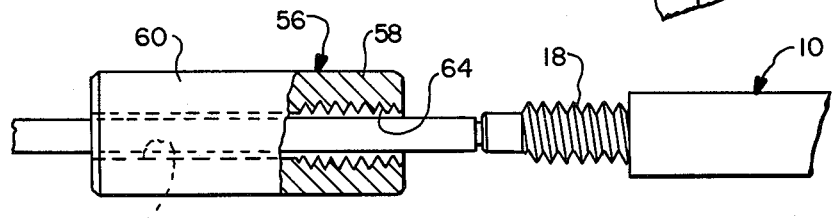
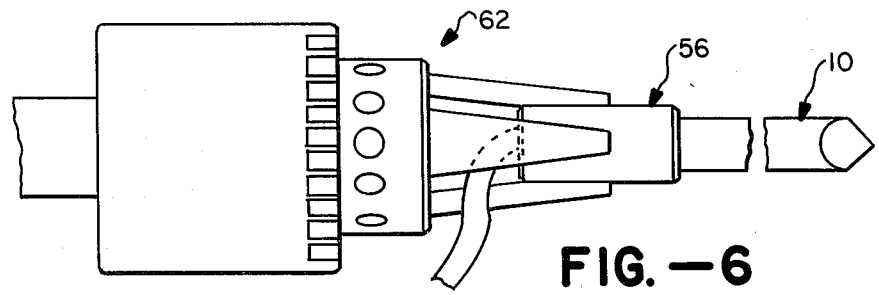

BONE AND TISSUE HEALING DEVICE INCLUDING A SPECIAL ELECTRODE ASSEMBLY AND METHOD

The present invention relates generally to techniques for expediting the healing of bone or soft tissue fractures or defects in a patient and more particularly to a completely portable device for this purpose, specifically one including a specially designed cathode electrode assembly.

The utilization of electric current to aid in expediting the healing of bone fractures or bone defects in a patient is well known in the art and has been the subject of numerous publications. One particular device or system is described in U.S. Pat. No. 3,842,841 (Brighton et al). The system disclosed there utilizes a cathode electrode and an anode electrode in combination with a direct current power supply and suitable circuitry for directing constant DC current into the fracture or defect site. This is accomplished by placing one of the electrodes, specifically the cathode electrode, in the patient at the fracture or defect site while the other electrode, specifically the anode electrode, is placed against the outer skin of the patient but otherwise in close proximity to the cathode electrode. This device is also described in a publication entitled THE ALTERNATE TREATMENT OF FRACTURE NON-UNION which discusses the ZIMMER (a registered trademark) direct current bone growth stimulator manufactured under a license of the Brighton et al patent.

Another device utilized to aid in expediting the healing of bone or soft tissue fractures or defects in a patient is described in Christensen et al U.S. patent application Ser. No. 340,520, filed Jan. 18, 1982 and entitled A PORTABLE, CONTINUOUSLY SELF-MONITORING BONE HEALING DEVICE AND METHOD which is copending with the present application and which has been assigned to assignee of the present application. This particular device is not only portable but continuously self-monitoring so as to always apprise the patient carrying the device of its operative status. In addition, this device and the ZIMMER device described in the publication cited above utilize rigid cathode electrodes which are located partially within and partially outside the patient. Because of its rigidity this type of electrode does not provide the necessary give to accommodate the differential movement between the patient's skin and tissue surrounding the electrode. More specifically, applicant has found that a rigid electrode which is only partially inserted into the patient tends to stretch and tear the opening in the skin around it, thereby preventing the latter from healing and increasing the possibility of infection.

In view of the foregoing, it is one object of the present invention to eliminate the problem just recited by providing an electrode assembly which includes a relatively rigid cathode electrode but which does not require that the electrode extend only partially into the patient.

A more specific object of the present invention is to provide an electrode assembly of the last mentioned type including a cathode electrode which is placed entirely within the patient but which is electrically connected with externally located circuitry without causing damage to the surrounding skin and tissue.

Another specific object of the present invention is to provide an uncomplicated technique for placing the last mentioned cathode electrode into its operating position entirely within the patient while a flexible electrical lead wire extends from the electrode to an external point through the skin of the patient for connection with cooperating circuitry.

As will be described in more detail hereinafter, the device for expediting the healing of bone and soft tissue fractures or defects disclosed herein is one which utilizes at least one cathode electrode and an anode electrode. This device also uses means including an electrical power supply for applying a regulated flow of current between the electrodes and into the fracture or defect site when the electrodes are placed in their operating positions. The cathode electrode is comprised of a rigid, electrically conductive shaft which is configured so as to be drilled into the fracture or defect site starting at its front end by using a compatible drilling device. A flexible electrical lead wire is mechanically and electrically connected at one end to the back end of the shaft within the patient and extends to an external point through the patient's tissue and skin where it is electrically connected to a cooperative circuit arrangement. Because of its flexibility, the section of lead wire disposed within the patient accommodates the differential movement between the surrounding skin and tissue of the patient for minimizing damage to the latter during such movement.

In a preferred embodiment of the present invention, the cathode shaft includes a threaded back end section for thread connecting to the cooperating threaded end of a drive member especially designed for use with a cooperating drilling device. In the preferred embodiment, this drive member is configured as a rigid, open ended tube threaded at its front end and having a through bore sufficiently large to accommodate the flexible lead wire recited above. In this way, the front end of the drive member can be connected to the back end of the cathode shaft while, at the same time, the lead wire extends through the drive member and in mechanical and electrical engagement with the shaft. As a result, the cathode electrode can be placed into position within the patient with the lead wire connected thereto.

The overall device including its cathode electrode assembly and the preferred way of placing the cathode electrode into position within the patient will be discussed in more detail below in conjunction with the drawing wherein:

FIG. 1 is a plan view of the cathode electrode forming part of the overall device and designed in accordance with the present invention;

FIG. 2 is a side view of a front end portion of the electrode illustrated in FIG. 1, taken generally along the line 2—2 in FIG. 1;

FIG. 3 is an enlarged, partially broken away plan view of an electrode assembly designed in accordance with the present invention and including the cathode electrode illustrated in FIG. 1;

FIG. 4 diagrammatically illustrates the entire device for expediting the healing of bone or soft tissue fractures or defects including the cathode electrode assembly of FIG. 3 in operating position;

FIG. 5 is an enlarged plan view of the assembly shown in FIG. 3 including an additional component, specifically a drive member adapted for connection with the cathode electrode and especially designed for use with a drilling device so as to drill the electrode into position at the fracture or defect site; and FIG. 6 diagrammatically illustrates how the combination cathode electrode assembly including the drive member illustrated in FIG. 5 is disposed within a drill chuck.

Turning now to the drawings, wherein like components are designated by like reference numerals throughout the various figures, attention is first directed to FIGS. 1 and 2 which illustrate a cathode electrode generally indicated by the reference numeral 10. This electrode is designed in accordance with the present invention for use in and as part of an overall device 12 (see FIG. 4) for expediting the healing of bone or soft tissue fractures or defects in a patient.

As shown in FIGS. 1 and 2, cathode electrode 10 (hereinafter merely referred to as a cathode) includes a metal or similar rigid, electrically conductive elongated shaft 14 which has a somewhat pointed front end section 16 and which is designed for drilling into relatively hard material, specifically the bone of a patient. The shaft is preferably circular in cross section along most of its length and includes an externally threaded back end section 18 which is provided for reasons to be discussed hereinafter. For the moment, it suffices to say that threaded section 18 is coaxial with the rest of the shaft and may be smaller in cross section than the main body of the shaft (as shown) or it may be larger. As seen in FIG. 1, threaded section 18 includes a central well 20 extending therein from its back end 22.

Referring to FIG. 3, cathode 10 is shown as part of an overall cathode electrode assembly which is generally indicated at 24. This assembly not only includes the cathode but also an electrically conductive, flexible lead wire 26 smaller in cross-section than the maximum cross-section of the cathode and an electrically conductive plug 28. As shown in FIG. 3, a front end section of the flexible lead wire is disposed within well 20 and is both electrically and mechanically connected with the cathode electrode, as indicated at 30. While any suitable means of connection may be utilized, the front end of the lead wire is preferably welded to the cathode at the end of well 20 by means of electron beam welding, resistance welding, or by any other suitable welding process. Plug 28 is disposed over a back end section of the flexible lead wire and electrically and mechanically connected thereto by any suitable means such as the double crimps indicated at 32. As will be seen hereinafter, the rearwardmost end section 34 of plug 28 is designed to electrically connect into cooperating circuitry forming part of the overall device 12, as will be discussed below.

Turning to FIG. 4, attention is directed to device 12 which, as stated previously, is provided for healing bone or soft tissue fractures or defects in a patient. The device is shown including cathode electrode assembly 24 as well as an anode electrode assembly 36 and a circuit arrangement 38. Both of these latter components, that is, the anode electrode assembly 36 and circuit arrangement 38 may be identical to the corresponding components forming part of the overall healing device described in the copending Christensen et al patent application recited above. At the same time, while cathode electrode assembly 24 differs structurally from the cathode electrodes forming part of the Christensen et al device, it functions in the same manner and electrically connects into arrangement 38 in the same way. Therefore, arrangement 38 serves to provide a regulated flow of current between the cathode and anode electrodes and through the fracture or defect site.

In FIG. 4, the cathode is shown embedded partially within the bone 40 of a patient's leg 42 adjacent a fracture site 44. The anode electrode assembly includes an anode electrode 46 which is placed in direct contact with the patient's skin in close proximity to the fracture site. As a result, current provided by arrangement 38 goes between the two electrodes through site 44, in the manner described in the Christensen et al patent application.

Electrode assembly 36 and circuit arrangement 38 may be identical to the corresponding components forming part of the healing device described in the copending Christensen et al patent application recited above. Accordingly, these components will not be discussed in detail. It suffices to say that the anode electrode 46 forming part of assembly 36 is one which is designed for external electrical connection with the patient's skin. This electrode is electrically connected into arrangement 38 by means of a lead wire 48 which is preferably flexible and an electrically conductive plug 50 which may be identical to plug 28 for plugging into the appropriate terminal in arrangement 38. This latter arrangement includes the necessary circuitry to produce the previously recited regulated flow of current and preferably includes the necessary means for making the device continuously self-monitoring as described in the Christensen et al patent application. As a result, arrangement 38 is shown including an outer casing 52 including a viewing window 54 through which a liquid crystal display may be observed for indicating the operative status of certain parameters, as discussed in the Christensen et al patent application. Also, overall device 12 as shown in FIG. 4 could include a plurality of cathode electrode assemblies as in the Christensen et al application.

As illustrated in FIG. 4, cathode 10 extends only partially within the patient's bone 40 but is disposed entirely within leg 42. A back end segment of the cathode including threaded section 18 is located outside the bone but inwardly from the patient's skin. Flexible lead wire 26 extends from the back end of the cathode to externally located plug 28 through the tissue and skin of the patient's leg. Applicant has found that when the patient moves his leg the skin and tissue surrounding the internal section of lead wire 26 move relative to one another. However, applicant has also found that by placing the relatively rigid cathode entirely within the patient's leg and connecting it to external plug 28 by means of a flexible lead wire which extends through the tissue and skin, the lead wire is able to accommodate this differential movement between the skin and tissue for minimizing damage thereto as a result of tearing or pulling. This is to be contrasted with the utilization of a rigid cathode extending through the skin and tissue of the patient which does not accommodate the differential movement between the two, as discussed above.

Having described cathode electrode assembly 24 and the way in which it is used to minimize damage to the skin and tissue surrounding it, attention is directed to the way in which the cathode is placed into the operating position illustrated in FIG. 4. In order to do this in accordance with the present invention, the overall cathode electrode assembly 24 includes what may be referred to as a drive member generally indicated at 56 in FIG. 5. As will be seen below, a front end section 58 of the drive member is designed for fixed but disengageable connection with the back end of cathode 10 and a back end section 60 of the drive member is designed to fit within a chuck 62 (see FIG. 6) of the drilling device, for example, a standard power drill. In this way, cathode 10 may be drilled into its position shown in FIG. 4 with lead wire 26 connected thereto.

The drive member 56 may be constructed of any suitable rigid material such as hard plastic or metal and is shown in FIG. 5 as an open ended cylindrical tube including previously recited front end section 58 and back end section 60. For the reasons to become apparent hereinafter, the opening through the tubular drive member which is generally indicated at 62 is at least slightly larger in cross section than lead wire 26 and plug 28 so that each can be threaded therethrough. Front end section 58 of the drive member is internally threaded at 64 in a way which allows the front end section to be thread connected to the externally threaded section 18 of cathode 10. In this regard, the cooperating threads of the two sections are designed so that when the drive member is rotated in the drill chuck 62 the two sections do not unthread from one another.

Returning to FIG. 4 in conjunction with FIG. 6, attention is now directed to the way in which the cathode 10 is placed into position within the patient's leg 42. At the outset it should be noted that the flexible lead wire 26 is initially electrically and mechanically connected to the back end of the cathode in the manner described previously. In addition, the plug 28 is preferably electrically and mechanically connected to the back end of the lead wire initially, athough as will be pointed out, this is not essential as an initial step in the precedure. However, for the moment, it will be assumed that the overall cathode electrode assembly is initially provided as shown in FIG. 3.

Thereafter, the drive member is threaded over the plug and flexible lead wire with its front end closest to the back end of the cathode as seen in FIG. 5. Once this is accomplished, the drive member and cathode are threaded together in a manner described previously. Thereafter, the back end section 60 of the drive member is placed in drill chuck 62 in the manner shown in FIG. 6. In placing the drive member in the chuck, it should be noted that the flexible lead wire 26 and plug 28 must be taken into consideration. More specifically, these two components will not fit within a standard drill chuck and hence must extend outwardly therefrom as shown in FIG. 6. While not shown, the section of lead wire extending outwardly from the chuck and the plug can be wound around the chuck or drive member for rotation therewith. On the other hand, a specially designed chuck may be readily provided to accommodate the lead wire and plug, for example within an internal compartment, although this would result in a relatively large chuck.

Once the drive member is disposed within the chuck, the cathode is now ready to be drilled into position within the patient's bone. Conventional means such as X-rays or the like are utilized during the positioning procedure to assure the appropriate placement of the cathode which is preferably such that most but not all of shaft 14 extends within the bone. At the same time, as stated previously, the entire cathode is disposed within the patient's leg. Also, as indicated by dotted lines in FIG. 4, once the cathode is in position, drive member 56 extends partially within and is located partially outside the patient's leg. In this regard, it should be noted that the outermost cross section of the drive member is shown to be slightly greater than the outermost cross section of cathode 10. This is a preferred configuration so that should the cathode be inadvertently drilled entirely into bone 40 the outermost circumferential section which forms part of the front end of the drive member outwardly of the cathode will cause the drive member to sufficiently resist entering the bone to alert the individual operating the drill. In this way, the drive member provides a means of limiting penetration of cathode 10.

Once cathode 10 is in position within bone 40, drive member 56 is disconnected from the cathode and removed from the patient's leg. Thereafter, it is entirely removed from lead wire 26 and plug 28 by moving it rearwardly over each of these components. At this time, the plug 28 can be connected into arrangement 38. In this latter regard, it should be apparent that cathode 10 could be placed into position as described above with lead wire 26 connected thereto but without plug 28. The plug could be connected to the back end of the lead wire after drive member 56 is removed therefrom. In this case, the cross section of opening 62 through the drive member need only be slightly larger than the lead wire and would not have to accommodate the plug.

Having described overall cathode electrode assembly 12 and the specific way in which the cathode 10 is placed into position within bone 40 utilizing a suitable drilling device including chuck 62, it is to be understood that the cathode can be placed into surrounding tissue in the same manner. Moreover, it is to be understood that while the specific drilling process for placing the cathode in its operative position forms one aspect of the present invention, the overall cathode electrode assembly including its flexible lead wire extending partially into and partially outside the patient and the cathode itself form other aspects of the present invention and that these aspects of the present invention are not limited to the specifically disclosed way in which the cathode is placed into operative position. Further, it is to be understood that, while overall device 12 has been shown including only one cathode electrode assembly, the device could and most likely would utilize a number of these assemblies as in the Christensen et al copending patent application recited previously.

Finally, without intended to limit the present invention, attention is now directed to an actual working embodiment of cathode electrode assembly 24. In this embodiment, the cathode is slightly greater than one-half inch long from tip to tip and its central shaft section displays an outer diameter of about 0.045 inch. The overall threaded end section 18 is about 0.07 inch long. The cathode is constructed of stainless steel and its threaded back end section 18 and a small segment of the cylindrical shaft section adjacent section 18 are covered with a black teflon coating. Well 20 extends into section 18 approximately 0.05 inch. Flexible lead wire 26 is a 25-strand 316 stainless wire coated with teflon and is approximately 20 inches long. Plug 28 is also constructed of stainless steel and is disposed over a stripped end section of the flexible lead wire. The entire plug is about 1.5 inches and its outer diameter is about 0.02 inches while the outer diameter of the lead wire is about 0.01 inch. The drive member 56 is constructed of stainless steel and is 8 inches long. Its outer diameter is about 0.06 inch and opening 62 is at least about 0.03 inch, that is, sufficiently large to accommodate both lead wire 26 and plug 28 in this actual embodiment.

What is claimed is:

1. A cathode electrode assembly including a cathode electrode for use in a device which expedites the healing of bone or soft tissue fractures or defects in a patient and which includes said electrode assembly and an anode electrode as well as means including an electrical power supply to produce a regulated flow of current between the anode and cathode electrodes for application through the fracture or defect site, said cathode electrode assembly comprising: said cathode electrode including a rigid, electrically conductive shaft which has a threaded outer surface section and a pointed front end so as to be readily drilled into said fracture or defect site starting at its front end by using a compatible drilling device such that the entire shaft is disposed within said patient, said shaft also including a back end segment having a back end and a well opening therein from said back end; and a flexible electrical lead wire mechanically and electrically fixedly connected at one end to the back end of said shaft within said well before the latter is drilled into the patient, said lead wire being adapted for electrical connection at its opposite end to said means including said power supply.

2. An assembly according to claim 1 wherein said one end of said wire connects to said shaft within said well by means of welding.

3. An assembly according to claim 1 wherein the back end segment of said shaft includes said threaded outer surface section, said assembly including an opened, tubular drive member having an internally threaded front end section thread connected with the thread section of said shaft and a back end section configured to fit within a drill chuck, said drive member in cooperation with a drilling device including said chuck serving to drill said cathode electrode into said fracture or defect site.

4. An assembly according to claim 3 wherein said drive member includes a sufficiently large through opening along its length through which said lead wire extends whereby said lead wire can be threaded through said drive member.

5. A cathode electrode assembly including a cathode electrode for use in a device which expedites the healing of bone or soft tissue fractures or defects in a patient and which includes said electrode assembly and an anode electrode as well as means including an electrical power supply to produce a regulated flow of current between the anode and cathode electrodes for application through the fracture or defect site, said cathode electrode assembly comprising: said cathode electrode including a rigid, electrically conductive shaft which has a pointed front end adapted to be readily drilled into said fracture or defect site starting at its front end by using a compatible drilling device such that the entire shaft is disposed within said patient, said shaft also including a back end; a flexible electrical lead wire mechanically and electrically fixedly connected at one end to the back end of said shaft before the latter is drilled into the patient, said lead wire being adapted for electrical connection at its opposite end to said means including said power supply; and means for connecting the back end of said shaft with said lead wire connected thereto to said drilling device for operation thereby.

6. An assembly according to claim 5 wherein said connecting means includes a tubular drive member having an opening through which said lead wire extends.

7. A method of expediting the healing of bone or soft tissue fractures or defects in a patient, said method comprising the steps of:

providing a completely portable device including an elongated, rigid first electrode and a second electrode, means for producing a regulated flow of current, and a flexible electrical lead wire smaller in cross-section than the maximum cross-section of said first electrode, said wire being electrically and mechanically connected to said first electrode;

placing said first electrode entirely within said patient at the fracture or defect site with the lead wire connected thereto, through the patient's skin, such that said lead wire extends from said first electrode to an external point through the patient's skin;

electrically connecting said current producing means with said first electrode utilizing connecting means including said flexible electrical lead wire extending from the first electrode within the patient to said external point through the patient's skin, said flexible wire being capable of accommodating differential movement between the patient's skin and tissue surrounding the flexible wire as the patient moves whereby to minimize damage to the surrounding skin and tissue as a result of such movement;

placing said second electrode in physical electrical contact with said patient at a point in close proximity to said fracture or defect site; and electrically connecting said current producing means with said second electrode.

8. A method for using a device which expedites the healing of bone or soft tissue fractures or defects in a patient and which includes an anode electrode, a cathode electrode and means including an electrical power supply for applying a regulated flow of current between the electrodes and through the fracture defect site, said method serving to place said cathode electrode in position at said fracture or defect site and comprising the steps of:

providing said cathode electrode in the form of a rigid, electrically conductive shaft having a front end and a threaded back end section;

electrically and mechanically connecting one end of a flexible electrical lead wire to the back end of said shaft;

providing an open ended tubular drive member having an inner diameter along its entire length which is greater than the outer diameter of said lead wire, said drive member having a front section which is threaded so as to thread connect it to the threaded section of said shaft;

inserting the free end of said flexible lead wire through said drive member from the front end of the latter;

thread connecting the front end of said tubular drive member with the threaded section of said shaft;

thereafter placing a back end section of said drive member in the chuck of a compatible drilling device; and utilizing said drilling device, drilling said electrode into position in said fracture or defect site.

9. A method according to claim 8 wherein said electrode is drilled into said fracture or defect site entirely within the patient while said drive member extends partially within and partially outside said patient, said method including the steps of disconnecting said drive member from said drilling device and also said cathode electrode, removing the drive member from said patient and separating it from the lead wire by passing it over and beyond the free end of the latter.

10. A method for using a device which expedites the healing of bone or soft tissue fractures or defects in a patient and which includes an anode electrode, a cathode electrode and means including an electrical power supply for applying a regulated flow of current between the electrodes and through the fracture defect site, said method serving to place said cathode electrode in position at said fracture or defect site and comprising the steps of:

providing said cathode electrode in the form of a rigid, electrically conductive shaft having a front end and a back end section;

electrically and mechanically connecting one end of a flexible electrical lead wire to the back end of said shaft;

providing an open ended tubular drive member having an inner diameter along its entire length which is greater than the outer diameter of said lead wire, said drive member having a front section adapted to be disengagably connected with the back end section of said shaft;

inserting the free end of said flexible lead wire through said drive member from the front end of the latter;

connecting the front end of said tubular drive member with the back end section of said shaft;

thereafter placing a back end section of said drive member in the chuck of a compatible drilling device; and utilizing said drilling device, drilling said electrode into position in said fracture or defect site.

11. A method according to claim 10 wherein said electrode is drilled into said fracture or defect site entirely within the patient while said drive member extends partially within and partially outside said patient, said method including the steps of disconnecting said drive member from said drilling device and also said cathode electrode, removing the drive member from said patient and separating it from the lead wire by passing it over and beyond the free end of the latter.

* * * * *